United States Defensive Publication [19] (H) [11] T979,004

Jamieson [43] Feb. 6, 1979

[54] N,N-BIS-(2-CARBOXYETHYL)-AMINO-PHENOLS

[75] Inventor: Norman C. Jamieson, St. Louis County, Mo.

[73] Assignee: Mallinckrodt, Inc., St. Louis, Mo.

[21] Appl. No.: 877,922

[22] Filed: Feb. 15, 1978

[51] Int. Cl.[2] ..... C07C 51/00

[52] U.S. Cl. ..... 562/452

[57] ABSTRACT

N,N-bis-(2-carbomethoxyethyl)-p-aminophenol is prepared by refluxing an aqueous solution of p-aminophenol and at least two molar proportions of acrylic acid to form N,N-bis-(2-carboxyethyl)-p-aminophenol, separating the N,N-bis-(2-carboxyethyl)-p-aminophenol and refluxing it with an excess of methanol in the presence of sulfuric acid to form N,N-bis-(2-carbomethoxyethyl)-p-aminophenol and isolating the N,N-bis-(2-carbomethoxyethyl)-p-aminophenol in relatively pure form.

10 Claims, No Sheets Drawing,

8 Pages Specification

The file of this unexamined application may be inspected and copies thereof may be purchased (849 O.G. 1221, Apr. 9, 1968).